United States Patent
Mc Culloch et al.

(10) Patent No.: US 6,548,721 B1
(45) Date of Patent: Apr. 15, 2003

(54) HYDROTREATING OLEFIN STREAM WITH COMPLETE DESTRUCTION OF OXYGENATES

(75) Inventors: Beth Mc Culloch, Clarendon Hills, IL (US); Jennifer L. Gordon, Palatine, IL (US); Peter Kokayeff, Naperville, IL (US); Suheil F. Abdo, Lincolnshire, IL (US); Daniel H. Wei, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/862,897

(22) Filed: May 22, 2001

(51) Int. Cl.$^7$ ................ C07C 5/02; C07C 5/03
(52) U.S. Cl. .......................... 585/277; 585/276
(58) Field of Search ................ 585/276, 277, 585/804

(56) References Cited

U.S. PATENT DOCUMENTS

| | | | |
|---|---|---|---|
| 2,526,966 A | 10/1950 | Oberfell et al. | 196/1 |
| 4,104,152 A | * 8/1978 | Hilfman | 208/108 |
| 4,244,806 A | 1/1981 | Le Page et al. | 208/49 |
| 4,304,948 A | 12/1981 | Vora et al. | 585/315 |
| 4,393,259 A | 7/1983 | Ward et al. | 585/315 |
| 4,749,820 A | 6/1988 | Kuo et al. | 585/330 |
| 4,950,820 A | * 8/1990 | Schleppinghoff et al. | 585/264 |
| 5,049,360 A | 9/1991 | Harandi et al. | 422/141 |
| 5,811,608 A | 9/1998 | Stine et al. | 585/316 |
| 5,847,252 A | 12/1998 | Stine et al. | 585/330 |
| 5,856,604 A | 1/1999 | Stine et al. | 585/310 |
| 5,877,372 A | 3/1999 | Evans et al. | 585/510 |
| 5,895,830 A | 4/1999 | Stine et al. | 585/259 |
| 5,990,367 A | 11/1999 | Stine et al. | 585/514 |
| 6,080,903 A | 6/2000 | Stine et al. | 585/514 |
| 6,329,561 B1 | 12/2001 | Webber et al. | 585/809 |

FOREIGN PATENT DOCUMENTS

EP    0 994 088 A1    4/2000

OTHER PUBLICATIONS

Paper entitled "InAlk™—The Flexible Route to Premium Alkylate" byL.O. Stine et al., presented at CatCon 2001, May 14–15, 2001.
Article "Optimize Alkylate Production for Clean Fuels" by J.M. Meister et al., *Hydrocarbon Processing*, May 2000, pp. 63–75.
Paper "Making Premium Alkylate with Your MTBE Unit" by J.M. Meister et al. presented at the Hart's World Fuels Conference, San Antonio, Texas, Mar. 28–30, 2000.

\* cited by examiner

*Primary Examiner*—Thuan D. Dang
(74) *Attorney, Agent, or Firm*—John G. Tolomei; James C. Paschall

(57) ABSTRACT

Disclosed is a process for completely destroying oxygenates in a feed stream. The feed stream of oxygenates typically includes olefins and it is reacted with hydrogen over a catalyst comprising a top row of Group VIII metal and a Group VI-B metal. Olefins are essentially completely saturated and any sulfur compounds present in the feed are completely converted to hydrogen sulfide. A preferred catalyst includes 2 to 5 wt-% nickel, 5 to 15 wt-% molybdenum, at least 5.5 wt-% sulfur, less than 0.05 wt-% phosphorus and no more than 0.3 wt-% silicon. The catalyst has low acidity and therefore does not promote the cracking of desired oligomeric products. The deoxygenation process is preferably a saturation process that follows an oligomerization process in which light olefins are oligomerized to heavy olefins. The saturation catalyst preferably has lower acidity which causes minimal cracking of desired oligomeric products. However, by optimally raising the temperature of the outlet of the saturation reaction zone, excessively heavy oligomers can be cracked down to desirable heavy oligomers.

19 Claims, 4 Drawing Sheets

HYDROTREATING OLEFIN STREAM WITH COMPLETE DESTRUCTION OF OXYGENATES

FIELD OF THE INVENTION

This invention relates to a process for saturating an oxygenate containing stream to destroy substantially all oxygenates. Moreover, this invention relates to saturating essentially all olefins in the oxygenate containing stream.

BACKGROUND OF THE INVENTION

Processes for the oligomerization of light olefins to produce heavy olefin oligomers are known. Oligomerization processes have been long employed to produce high quality motor fuel from $C_4$ olefins. Such oligomerization processes are also referred to as catalytic condensation and polymerization with the resulting motor fuel often referred to as polymer gasoline. Methods have always been sought to improve the octane number of the gasoline boiling range oligomerization products.

In the oligomerization method of the indirect alkylation process set forth in, for example, U.S. Pat. Nos. 6,080,903 B1, 5,990,367 B1 and 5,895,830 B1, light aliphatic olefins such as $C_4$ olefins are contacted with solid phosphoric acid (SPA) catalyst in the presence of a heavy paraffin diluent such as cyclohexane or isooctane. The presence of the paraffin diluent is believed to promote the oligomerization in the liquid phase to yield predominantly dimerized oligomers such as $C_8$ olefins. Light paraffinic feed can be dehydrogenated to provide the feed for the indirect alkylation process. Patents disclosing such dehydrogenation include U.S. Pat. Nos. 4,393,259 B1, 5,049,360 B1, 4,749,820 B, 4,304,948 B1 and 2,526,966 B1.

Other oligomerization processes using an ionic exchange resin catalyst to oligomerize light olefins to produce oligomers such as $C_8$ olefins are also known. These processes often include an oxygenate such as tert-butyl alcohol (TBA) or sec-butyl alcohol (SBA) in the feed for modifying the catalyst to maintain desired selectivity. When water is added to feed containing $C_4$ olefins, it reacts with $C_4$ olefins to generate TBA and SBA which moderate the resin catalyst. References disclosing resin catalyzed oligomerization include U.S. Pat. No. 5,877,372 B1 and EP 0994088 A1. A dehydrogenation zone to convert paraffinic feed into olefinic feed can also precede the resin catalyzed oligomerization.

The oligomerization of $C_4$ olefins across an acidic catalyst such as SPA produces a variety of $C_8$ olefins. When the feed contains only isobutylene, the predominantly produced olefin is 2,4,4-trimethylpentene which can be saturated to 2,2,4-trimethylpentane. Normal butenes present in the feed oligomerize to produce $C_8$ olefins such as 2,2,3-trimethylpentene and dimethylhexenes. Secondary reactions can also occur in which 2,4,4-trimethylpentene product isomerizes through a methyl shift to give 2,3,4-trimethylpentene or 2,2,3-trimethylpentene and dimethylhexenes. Additionally, $C_4$ olefins can also trimerize to produce triisobutane after saturation.

Table 1 gives the octane numbers and boiling points for $C_8$ isomers and for $C_{12}$.

TABLE 1

| Isomer | Research Octane Number | Motor Octane Number | Boiling Point at 1 atm (° C.) |
|---|---|---|---|
| 2,2,4-trimethylpentane | 100 | 100 | 99.2 |
| 2,3,4-trimethylpentane | 102.7 | 95.9 | 113.5 |
| 2,2,3-trimethylpentane | 109.6 | 99.9 | 109.8 |
| 2,3,3-trimethylpentane | 106.1 | 99.4 | 114.8 |
| 2,2-dimethlyhexane | 72.5 | 73 | 106.7 |
| 2,3-dimethylhexane | 91.1 | 88.5 | 115.6 |
| Triisobutane | 95 | 90 | 216 |

Product oligomers with higher octane numbers and lower boiling points are the most preferred. Accordingly, 2,2,4-trimethylpentane is the most preferred $C_8$ isomer; whereas, 2,3,4-trimethylpentane and 2,3,3-trimethylpentane are the least preferred $C_8$ isomers because of their high boiling point temperature. The dimethylhexanes are undesirable because of their low octane numbers and relatively high boiling points and triisobutane is undesirable because of its very high boiling point temperature.

U.S. Pat. Nos. 5,856,604 B1, 5,847,252 B1 and 5,811,608 B1 teach succeeding such oligomerization processes with a saturation reaction zone to convert heavy oligomeric olefins into heavy alkanes that can be blended with gasoline stock. Saturation is known to be particularly beneficial when saturating isooctenes to isooctane gasoline. These patents disclose using a catalyst comprising a metal from a top row of Group VIII of the Periodic Table of the Elements such as nickel and a metal from Group VI-B of the Periodic Table of the Elements such as molybdenum in the saturation reaction zone. However, they indicate no appreciation of the effectiveness of such catalysts with respect to oxygenates and the criticality of properly preparing the catalyst.

One must be careful to avoid catalysts for saturating oligomerized olefins to make gasoline fractions that can lower octane ratings and excessively lower the boiling point down to the range of $C_4$ hydrocarbons. For instance, saturation catalysts can crack $C_8$ hydrocarbons down to $C_4$ hydrocarbons which degrades product quality by lowering the octane rating. On the other hand, cracking of $C_{12}$ or heavier hydrocarbons down to lighter hydrocarbons in a saturation unit would be desirable. Saturation catalysts that isomerize $C_8$ hydrocarbons to a $C_8$ isomer that has a lower octane number and/or higher boiling point are less desirable.

Saturation processes are typically required to meet certain high level of conversion of olefin to alkane. For example, future gasoline specifications are expected to require a very low level of olefins in the pool. The saturation process must be able to sufficiently convert isooctenes to meet these requirements. Moreover, if unreacted pure isobutene is subjected to saturation for recycling in a process where isobutane is oxidized to obtain tert-butyl hydroperoxide, the recycled isobutane must contain less than 100 ppm isobutylene. In addition, in such a process, the isobutane stream may contain no sulfur and essentially no oxygenates. Hence, high conversion in the saturation process is very important.

U.S. Pat. No. 4,244,806 B1 discloses hydrogenating a stream of isobutene dimers and trimers over a nickle or noble metal catalyst on a non-acidic carrier such as alumina. However, noble metal catalysts are sensitive to the presence of oxygenates and sulfur compounds in the hydrogenation stream. Oxygenates are compounds that contain oxygen such as alcohols, ethers, ketones, aldehydes or water. Notable sulfur compounds include mercaptans and dimethyl disulfides. To avoid diminishing noble metal catalyst activity, a hydrogenation feed may have-to be purified of sulfur through a sulfur unit, thereby increasing the capital cost required to operate with a noble metal catalyst. Furthermore, the hydrogenation feed may have to be purified of oxygenates by running it through at least one oxygenate removal unit (ORU) containing adsorbent to adsorb the oxygenate. Such ORU's must be shut down periodically to regenerate the adsorbent requiring installation of an additional ORU or substantial down time. Additionally, a large volume of regenerant for regenerating the adsorbent must be obtained and disposed of periodically. The elimination or substantial reduction of oxygenates is becoming more important because of recent governmental regulations to decrease or eliminate- the use of methyl tert-butyl ether (MTBE) as a gasoline blending component and heightened environmental concern over the effects of oxygenates. Methods of removing oxygenates will become more useful because oligomerizing $C_4$ olefins over resin catalyst can produce as much as 5 wt-% $C_8$ ethers.

Hence, it is an object of the present invention to provide a saturation process that uses a catalyst that can withstand sulfur and oxygenates in the feed. It is a further object of this invention to provide a saturation process that uses a catalyst that essentially saturates all olefins. It is a still further object of the present invention to provide a process that destroys all oxygenates and converts sulfur compounds into easily managed hydrogen sulfide. It is an even further object of the present invention to provide a saturation process that minimally degrades product quality.

SUMMARY OF THE INVENTION

We have discovered a process that utilizes a catalyst comprising a top row Group VIII metal and a Group VI-B metal, such as a nickel-molybdenum catalyst, to completely destroy all oxygenates, essentially completely saturates all olefins and converts all sulfur compounds to hydrogen sulfide which can be removed in an overhead of a distillation column, thereby excluding sulfur compounds from the gasoline pool. Additionally, we have found that a sufficiently sulfided nickel-molybdenum catalyst has sufficient activity but with sufficiently low acidity to optimize cracking and minimize isomerization to obtain high quality saturate product.

In one embodiment, the present invention relates to a process for producing heavy alkanes from light olefins. The process comprises passing a feed stream containing light olefins to an oligomerization zone. The feed stream is contacted with an oligomerization catalyst to produce heavy olefins. An oligomerization effluent from the oligomerization reactor containing heavy olefins and oxygenates is passed to a saturation reactor. The oligomerization effluent is contacted with hydrogen in the presence of a saturation catalyst comprising a metal from a top row of Group VIII of the Periodic Table of the Elements and a metal from Group VI-B of the Period Table of the Elements in the saturation reaction zone to produce heavy alkanes. A saturation effluent is recovered from the saturation reaction zone containing less than 100 ppm of oxygenates.

In another embodiment, the present invention relates to a process for saturating olefins comprising feeding a saturation stream containing olefins and oxygenates to a saturation reaction zone. Hydrogen is fed to the saturation reaction zone. The saturation stream is contacted with a saturation catalyst comprising a metal from a top row of Group VIII of the Periodic Table of the Elements and a metal from Group VI-B of the Periodic Table of the Elements. An effluent is recovered from the saturation reaction zone comprising less than 100 ppm of oxygenates.

In a further embodiment, the present invention relates to a process for deoxygenating a stream containing oxygenates. The process comprises feeding hydrogen and a stream containing oxygenates to a deoxygenation zone. The feed stream is contacted with a catalyst comprising a metal from a top row of Group VIII of the Periodic Table of the Elements and a metal from Group VI-B of the Periodic Table of the Elements. An effluent is recovered from the deoxygenation zone comprising less than 100 ppm of oxygenates.

Additional objects, embodiments and details of this invention can be obtained from the following detailed description of the invention.

DETAILED DESCRIPTION OF THE INVENTION

Figure 1:
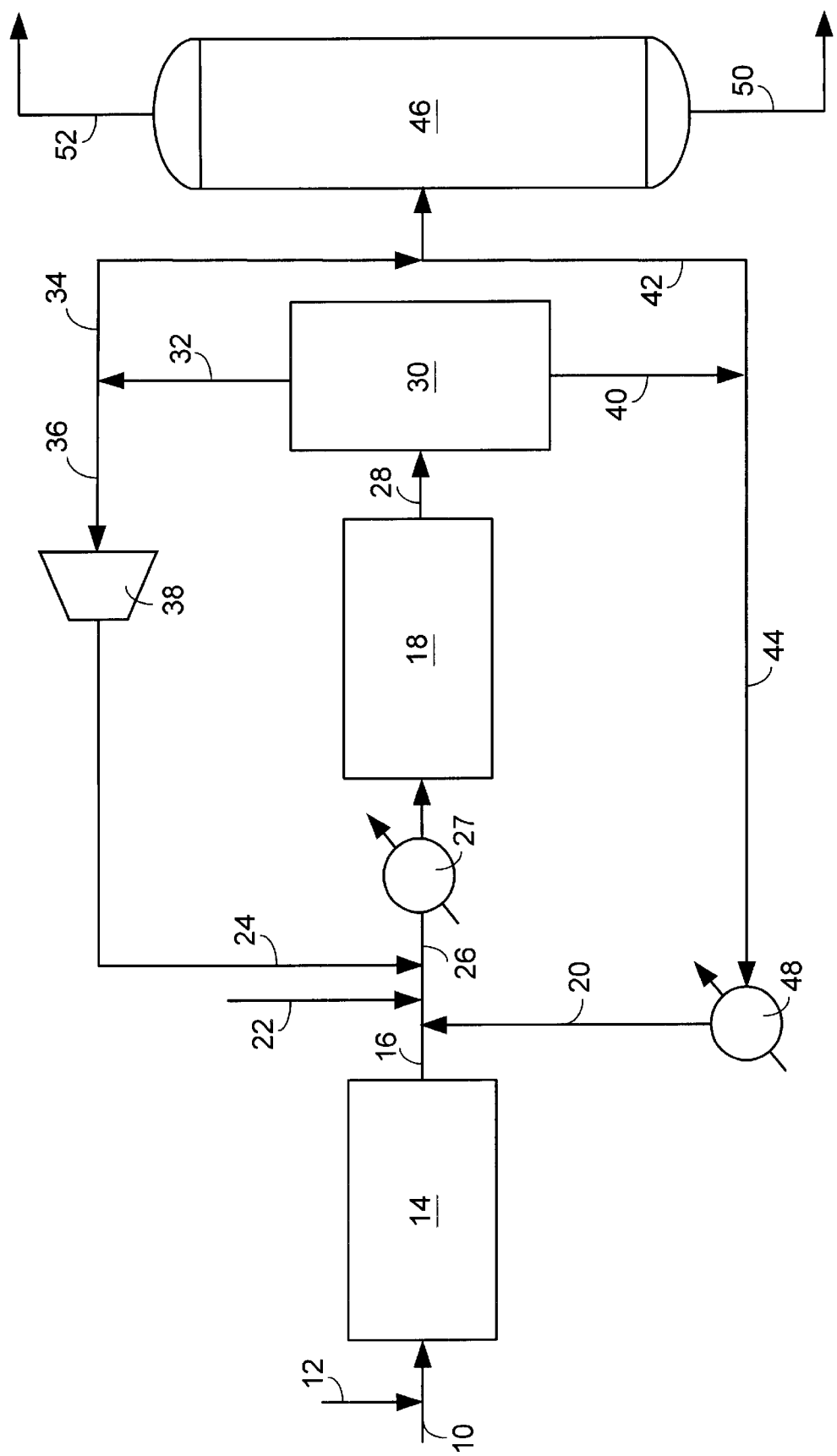
FIG. 1 is a schematic process flow scheme for an oligomerization process of the present invention.

The present invention can be used to completely destroy oxygenates and to essentially completely saturate olefins in an effluent from an oligomerization reaction zone. The invention is particularly useful in the saturation of $C_8$ olefins made by dimerizing $C_4$ olefins for the production of gasoline. Hence, for illustrative purposes, the invention will be described in the context of the production of $C_8$ hydrocarbons, but the invention is not so limited.

In such an oligomerization process, a source of olefins is delivered to an oligomerization reactor in which the light olefins oligomerize over either an SPA catalyst, a resin catalyst or another appropriate catalyst to form heavier oligomers. The oligomerization effluent is then at some point mixed with hydrogen and reacted over a saturation catalyst to convert the heavy oligomer olefins to heavy oligomer alkanes for subsequent blending in a gasoline pool. The present invention focuses on the saturation reaction zone.

We have found that a catalyst comprising a top row Group VIII metal such as nickel and a Group VI-B metal such as molybdenum can be used in the saturation process to replace noble metal catalysts at conditions that are compatible with conditions under which the indirect alkylation process is operated. The preferred nickel-molybdenum catalyst is not sensitive to sulfur and oxygenates like the conventional noble metal catalysts and we have found unexpectedly that it completely destroys all oxygenates fed to the saturation reactor. Complete destruction of oxygenates means that no oxygenates are detected in the effluent from the saturation reactor down to a detection limit of 1 ppm. However, concentrations of oxygenates below 100 ppm are typically insignificant. Hence, the need for an oxygen removal unit is eliminated which was previously necessary because of the sensitivity of the noble metal catalyst to oxygenates. Additionally, the saturation process of the present invention converts all sulfur compounds to hydrogen sulfide, again down to a detection limit of 1 ppm. Hydrogen sulfide can be removed in the overhead product of a distillation column and diverted from the gasoline pool. Accordingly, no separate sulfur treatment unit is required with the present invention. Lastly, the saturation process is capable of saturating olefins down to a level of 0.01 wt-%, which is essentially completely saturating the olefins. Therefore, there is no need to append an additional saturation finishing process onto the process of the present invention.

The oligomerization process that precedes the saturation process is known by many names such as catalytic condensation, catalytic polymerization and indirect alkylation. Preferred catalyst for the oligomerization reaction can generally be described as protonic acids. The preferred acids will generally have a Hammett acidity function of −4.0 or less. Examples of catalysts falling into this category include ion exchange resin catalysts, such as sulfonated ion exchange resins, and phosphoric acid catalysts. One particularly preferred catalyst is an SPA catalyst which has a Hammett acidity function of approximately −5.0 or lower. The SPA catalyst refers to a solid catalyst that contains as a principal ingredient an acid of phosphorus such as ortho-, pyro- or tetraphosphoric acid. Details as to the composition and production of SPA catalysts may be obtained from U.S. Pat. Nos. 3,050,472 B1, 3,050,473 B1 and 3,132,109 B1 and from other references.

Another particularly preferred catalyst is a sulfonic acid ion-exchange resin catalyst. This resin catalyst comprises sulfonic acid groups and can be prepared by polymerizing or copolymerizing aromatic vinyl compounds followed by sulfonating. Examples of aromatic vinyl compounds include the following: styrene, vinyl toluene, vinyl naphthalene, vinyl ethylbenzene, methyl styrene, vinyl chlorobenzene and vinyl xylene. An acidic ion-exchange resin contains typically approximately 1.3 to 2.0 sulfonic acid groups per aromatic group. Preferred resins are those based on copolymers of aromatic monovinyl compounds and aromatic polyvinyl compounds and in particular divinyl compounds in which the concentration of polyvinyl benzene is approximately 1 to 20 wt-% of the copolymer. The particle size of the ion-exchange resin is preferably approximately 0.15 to 1 mm. Furthermore, perfluorosulfonic acid resins consisting of copolymers of sulphonylfluorovinyl ethyl and fluorocarbon compounds can be used. Various suitable ion-exchange resins are commercially available under the name, for example, Amberlyst 15®. The concentration of the catalyst is typically 0.01 to 20% of the mixture it is treating and preferably 0.1 to 10% of the weight.

Oligomerization zones in general are maintained at conditions that may vary widely due to the previously listed variables. The temperature of the oligomerization reaction zone using SPA catalyst may be in a range of from 380 to 260° C. (1000 to 500° F.), will typically be in a range of from 93° to 260° C. (200° to 500° F.), and will preferably be in a range of from 93° to 177° C. (200° to 350° F.). We have found that for feeds with greater than 40 wt-% of isobutylene, the inlet temperature to the oligomerization reaction zone is preferably between 93° and 127° C. (200° and 260° F.). The outlet temperature from the oligomerization reaction zone with 40 wt-% isobutylene in the feed is preferably between 127° and 160° C. (260° and 320° F.). These lower temperatures prevent isooctene from cracking down to lighter olefins and the desired 2,4,4-trimethylpentene from undergoing a methyl shift to 2,3,4-trimethylpentene which has a high boiling point and a low motor octane number. These lower temperatures work best when the feed includes a high concentration of isobutene. Higher temperatures are needed to promote oligomerization if greater concentrations of normal butenes are in the feed. The temperature of the oligomerization reaction zone in which a resin catalyst is used is 0° to 200° C. (32° to 392° F.) and preferably 40° to 150° C. (104° to 302° F.).

Pressures within the oligomerization reaction zone using the SPA catalyst will usually be in a range of from 690 to 10342 kPa (100 to 1500 psig) and more typically in a range of from 1379 to 6895 kPa (200 to 1000 psig) with pressures of 1379 to 3447 kPa (200 to 500 psig) being particularly preferred. Pressures in the oligomerization zone using the resin catalyst will be sufficient to maintain the liquid phase, typically 345 to 3447 kPa (50 to 500 psig), and preferably 1380 to 2413 kPa (200 to 350 psig). Oligomerization conditions may also include a liquid hourly space velocity (LHSV) of 0.5 to 8 $hr^{-1}$ with 1 to 6 $hr^{-1}$ being preferred.

The feed to the oligomerization reaction zone will typically comprise $C_3$ to $C_5$ aliphatic olefins. Steam or water may be fed into the reactor to maintain a low water content for hydration of the SPA catalyst or to modify the resin catalyst.

The source of the olefin feeds are typically a light gas stream recovered from the gas separation section of an FCC process, $C_4$ streams from steam cracking and coker off gas, $C_3$ streams such as from a separator section of a modified FCC process or the effluent from a dehydrogenation zone. In most operations, this olefin feed stream will contain at least 10 wt-% $C_4$ olefins but it may also constitute all or substantial quantities of $C_3$ olefins. Typically the olefin feeds can have a $C_3$ to $C_5$ olefin concentration of at least 30 wt-%. Where $C_4$ olefins are predominant in the feed, the principal oligomerization products comprise $C_8$ and heavier olefins. Where $C_3$ olefins are predominant in the feed, these olefins will primarily combine to produce $C_9$ and higher olefins. Preferred feeds will have a concentration of at least 30 wt-% and more preferably at least 50 wt-% total olefins in the feed stream.

When using the SPA catalyst, a saturate stream comprising paraffin components contact the catalyst in conjunction with the usual oligomerization zone feed. The paraffin components will preferably comprise heavy hydrocarbons having at least 6 carbon atoms, preferably at least 7 carbon atoms, and more preferably at least 8 carbon atoms. Cycloparaffins are also suitable components for the saturate stream with cyclohexane being preferred. The presence of the heavy paraffins promotes liquid phase conditions in the oligomerization zone. The combined heavy saturate stream and feed will usually maintain at least partial liquid phase conditions in the oligomerization zone. Preferably, essentially all, i.e. at least 90 wt-%, of the fluid in the oligomerization zone will be in liquid phase. With the addition of the saturate stream, the combined feed to the oligomerization zone will preferably have a ratio of paraffins to olefins of from 1:1 to 8:1 with a ratio of 4:1 to 8:1 being preferred. Thus the overall paraffin concentration of the feed to the oligomerization reaction zone will typically be at least 50 wt-% and more typically at least 70 wt-%. An oligomerization reaction zone using a resin catalyst will not typically recycle a saturate stream. The olefin conversion in the oligomerization reaction zone will typically range from 80 to 99 wt-% and the oligomerization reaction product will principally comprise $C_6^+$ olefins.

The oligomerization effluent contains principally unreacted $C_4$ olefins, nonparticipatory light paraffins, olefinic gasoline components and in the case of an SPA catalyst in the oligomerization reactor, paraffinic components, and in the case of a resin catalyst in the oligomerization reactor, TBA, SBA and $C_8$ ethers. The effluent from the oligomerization zone will preferably pass directly to the saturation reaction zone without separation or recovery of light ends.

The saturation reactor will typically operate at higher temperatures than the oligomerization reactor so paraffins in the effluent from the SPA oligomerization reactor will provide additional heat sink material for the higher operating temperatures of the saturation reaction zone. If a resin catalyst is used in the oligomerization reactor, downstream product is recycled to the saturation reactor to provide heat sink material.

Before entering the saturation reaction zone the oligomerization effluent is first mixed with a hydrogen-containing gas stream, although hydrogen could be separately fed to the saturation reaction zone. The gas stream should contain at least 50 wt-% of hydrogen. Preferably, the hydrogen-containing gas stream will have a hydrogen concentration greater than 75 wt-% hydrogen. Hydrogen recovered from the dehydrogenation section, if a part of the oligomerization complex, may supply a major amount of the hydrogen fed to the saturation reaction zone with the remainder of the necessary hydrogen supplied from outside sources as a make-up hydrogen. High purity is preferred for the make-up hydrogen to increase the overall purity of the hydrogen entering the saturation reaction zone thereby reducing the volume of light hydrocarbons. These light hydrocarbons are undesirable since their presence needlessly increases the mass volume through the saturation reaction zone.

Hydrogen is recovered downstream of the saturation reaction zone and recycled to the saturation reactor to maintain a higher hydrogen-to-olefin ratio. When the hydrogen purity of the recycled hydrogen is low, the purity of hydrogen in the make-up gas stream must be proportionately higher. The make-up gas stream and the recycled hydrogen stream are mixed with the oligomerization effluent in proportions that will produce a hydrogen-to-olefin ratio in a range of 1.6:1 to 8:1 with 1.6:1 to 2.2:1 being preferred.

The saturation reactor of this invention will contain a catalyst to provide an essentially complete saturation of all unsaturated hydrocarbons. The combined feed to the saturation reactor is preheated to the saturation reaction temperature and fed to the saturation reactor. Conditions within the saturation reaction zone include an inlet temperature in the range of 204° to 260° C. (400° to 500° F.), with 232° C. (450° F.) being preferred. An outlet temperature for the saturation reaction zone in the range of 260° to 288° C. (500° to 550° F.) is suitable with 274° C. (525° F.) being preferred. We have found that at an outlet temperature of the saturation reaction zone of 274° C. (525° F.), the concentration of $C_{12}$ hydrocarbons in the product diminishes by 30%, from 12 wt-% to 9 wt-% $C_{12}$ hydrocarbons. Moreover, the $C_{12}$ hydrocarbons crack to isobutane and 2,2,4-trimethylpentane. This 30% reduction in $C_{12}$ hydrocarbons and increase in 2,2,4-trimethylpentane greatly improves the octane number of the product and significantly reduces the boiling point of the product advantageously. Although, raising the outlet temperature does have the undesired effect of cracking the product $C_8$ hydrocarbons in addition to the $C_{12}$ hydrocarbons, we have found that an outlet temperature of 274° C. (525° F.) is optimum for maximizing the cracking of $C_{12}$ hydrocarbons and minimizing the cracking of $C_8$ hydrocarbons.

The pressure in the saturation reaction zone is in the range of 1724 to 4482 kPa (250 to 650 psig), with less than 2413 kPa (350 psig) being preferred from an operational cost perspective. The LHSV of the saturation reaction of 3 to 15 $hr^{-1}$ is suitable and 5 to 8 $hr^{-1}$ is preferred. Preferably, the reaction conditions are selected to keep the hydrocarbon feed in a vapor phase. The saturation reaction zone will generally operate at temperatures that permit the raising of the combined feed stream to reaction temperatures by heating and recycling saturation effluent to the saturation reaction zone. In this manner, any heat importation into the oligomerization and hydrogenation sequence can preferably be made by a trim heater on the saturation effluent recycle stream.

The preferred saturation reactor contains a fixed bed of saturation catalyst. Combinations of nickel and molybdenum have been found to be particularly preferred saturation catalysts. The nickel should comprise 2 to 5 wt-% and the molybdenum should comprise 5 to 15 wt-% of the catalyst. Because of their similar characteristics, we also believe that other metals from a top row of Group VIII may be substituted for nickel and other metals from Group VI-B of the Periodic Table of the Elements can be substituted for molybdenum in similar proportions to obtain comparable performance. The metallic components are supported on a porous carrier material such as alumina. The weight percentages of the metals are calculated as though they existed in the metallic state. Typical commercial catalysts comprise spherical or extruded alumina based composites impregnated with nickel-molybdenum, for example, in the proportions suggested above. The average bulk density of the catalysts may range from 0.5 to 0.9 g/cc with surface areas ranging from 175 to 300 $m^2/g$.

We have found that it is desirable to minimize the acidity of the saturation catalyst because acidity can cause cracking and isomerization of oligomerization product which can degrade product quality. Although some cracking of heavier oligomers, such as triisobutylene, is desirable, cracking of isooctenes down to isobutene compounds tends to reverse what was achieved in the oligomerization process. Hence, if additional cracking of triisobutylene is desired, increasing the saturation reaction temperature is preferred over using an acidic saturation catalyst. We have found that high molybdenum levels in the catalyst, such as greater than 15 wt-% result in a high degree of cracking. Hence, the molybdenum level in the catalyst should be maintained between 5 and 15 wt-%. If another Group VI-B metal is used, a similar level of the Group VI-B metal in the catalyst should be maintained. We have also found that sufficiently sulfiding the catalyst to obtain a greater than or equal to 5.5 wt-% sulfur in the catalyst decreases the potential of the catalyst to crack desired product most significantly. We have also found that the higher levels of phosphorus raise the acidity level of catalyst to increase its cracking potential. Hence, the phosphorus level in the catalyst should be maintained at less than or equal to 0.1 wt-% and preferably less than or equal to 0.05 wt-%. Maintaining silica level in the catalyst is also important to decreasing the cracking potential of the catalyst. Silica levels should be maintained at less than or equal to 0.3 wt-% and preferably less than or equal to 0.2 wt-%. Among the four catalyst variables, it is most important to moderate the molybdenum level in the catalyst to decrease the tendency of the catalyst to crack. Of secondary importance is to keep the sulfur level high. Of tertiary importance is keeping the phosphorus level low. Of least importance is maintaining a low level of silica.

We also have discovered that catalyst with high acidity can cause isomerization of isooctene product down to $C_8$ isomers that are less desirable. We found that when phosphorus levels in the catalyst are high, 2,3,4-trimethylpentane and dimethylhexane are present in the product in higher concentrations. Dimethylhexanes have a low octane number. Although 2,3,4-trimethylpentane has a higher octane number, it has a relatively high boiling point which increases the boiling point of the product undesirably. Accordingly, the preferred catalyst for the present invention will have phosphorus concentration of less than 0.05 wt-%, a silica concentration of no more than 0.2 wt-%, a concentration of molybdenum between 5 and 15 wt-% and a sulfur concentration of at least 5.5 wt-%

A nickel-molybdenum catalyst of the present invention may be made by peptizing a pseudo-Boehmite with an appropriate amount of peptizing agent and adding sufficient water to produce a mixture characterized by a weight loss on ignition (LOI) at 900° C. (1652° F.) of from about 50 to 70%. The peptizing agent is suitably a weak acid such as formic acid, acetic acid, propionic acid and the like, although strong acids, for example, sulfuric acid, hydrochloric acid, and especially nitric acid, are preferred. The mixture is then kneaded and then mixed with $Ni(NO_3)_2.6H_2O$ and $(NH_4)_2Mo_2O_7$ and the resultant mixture is extruded at a size of $\frac{1}{16}$-inch in diameter. The extrudate is dried at 100° C. (212° F.) for 30 minutes and calcined by ramping the temperature to 250° C. (482° F.) for 15 minutes, to 500° C. (932° F.) for 50 minutes and then to 610° C. (1130° F.) for 100 minutes. During calcination, pseudo-Boehmite converts into γ-alumina crystal. The calcined extruded base contains.1.45 wt-% nickel and 3.35 wt-% molybdenum. The calcined extruded base is impregnated with $Ni(NO_3)_2.6H_2O$ and $(NH_4)_2Mo_2O_7$ in a 20 wt-% ammonia solvent having a 0.51 solution to base volume ratio and evaporated to 40% LOI to give the catalyst a composition of 3.6 wt-% nickel and 11.8 wt-% molybdenum. The impregnated calcined extruded base is then calcined at 210° C. (410° F.) for 50 minutes and at 550° C. (1022° F.) for 100 minutes.

A sulfur component is also preferably present in significant amounts only upon the surface of the alumina support. This component is preferably present in a concentration varying between about 3.0 to about 11.0 wt-%. A preferred range of the sulfur concentration in the subject catalyst is from 4.0 to 9.0 wt-% with it being highly preferred that the sulfur concentration in the finished catalyst is at least 5.5 wt-%. The sulfur component is preferably added to the catalytic composite in a final preparation step after the final calcination step. In the sulfiding procedure, the impregnated calcined extruded base composite is subjected to sulfiding conditions sufficient to provide the desired sulfur concentration. Sulfiding may be performed under liquid phase conditions; however, it is greatly preferred to perform this step at vapor phase conditions. It is therefore preferred to effect the deposition of the sulfur component upon the catalyst by contacting the initial composite with a vaporous sulfur-containing compound. Preferably, the sulfur-containing compound is present in admixture with hydrogen. A preferred sulfur-containing or sulfur-yielding compound is hydrogen sulfide. Other sulfur or sulfide-yielding compounds which may be employed for this purpose include ammonium sulfide, ammonium hydrosulfide, the alkyl and aryl mercaptans, organic thioethers, disulfides, thioaldehydes, and other sulfur-yielding organic compounds. The sulfiding conditions will therefore preferably include a temperature sufficient to maintain the sulfiding compound present as a vapor, with these temperatures ranging from about 10° to about 500° C. (50° to about 932° F.). A preferred range is from about 20° to about 450° C. (68° to about 842° F.) when hydrogen sulfide is utilized as the sulfiding agent. The pressure employed during the sulfiding step can be selected from an extremely broad range and does not greatly affect the course of the sulfiding step. Atmospheric pressure is preferred. The initial composite may be sulfided statically using hydrogen sulfide or in a flowing gas stream containing about 5 to about 30% hydrogen sulfide which is passed over the initial catalyst composite at a gas hourly space velocity (GHSV) of about 150 to 570 $hr^{-1}$. We have found that sulfiding in the presence of 10% hydrogen sulfide at 399° C. (750° F.) for six hours at a GHSV of 470 $hr^{-1}$ adequately sulfides the saturation catalyst.

Effluent from the saturation reaction zone enters a separator such as a flash drum. The flash drum is operated at a pressure range of 689 to 2413 kPa (100 to 350 psig) and a temperature range of 49° to 66° C. (120° to 150° F.). The separator sends hydrogen and some lighter components out the overhead to recycle the hydrogen to the saturation reactor and sends the majority of the effluent from the saturation reaction zone out the bottoms. The bottoms product of the separator is split with one stream having a relatively high concentration of heavy hydrocarbons being recycled upstream. If the oligomerization reactor zone uses an SPA catalyst, the heavy hydrocarbons are recycled to the oligomerization zone. If the oligomerization reactor zone uses a resin catalyst, the recycled heavy hydrocarbons are mixed with the feed for the saturation reaction zone to moderate the temperature therein. Except for any volume that is recycled, all of the remaining effluent from the saturation reaction zone will preferably enter a primary separation column. The saturation effluent contains no oxygenates above ppm detectable levels, contains no sulfur compounds above ppm detectable level other than hydrogen sulfide and is essentially free of olefins. The olefin concentration will be less than 0.1 wt-%, preferably less than 0.03 wt-% and can be as low as 0.01 wt-%.

In the primary separation column, the bottoms product will include the heavy alkanes comprising primarily $C_6$ and heavier alkenes which will be sent on for blending with the gasoline pool. This product stream will be free of sulfur compounds, oxygenates and essentially free of olefins. The overhead product will include light hydrocarbons, no oxygenates, an even lower concentration of olefins than in the bottoms product and hydrogen sulfide. All of the sulfur compounds fed to the saturation reaction zone will be converted to hydrogen sulfide which goes out the top of the distillation column. Therefore, the bottoms product will have no sulfur compounds, no oxygenates and very low olefin concentration, thereby providing a very high quality gasoline blending component.

The invention will now be described with respect to FIG. 1 which illustrates an oligomerization saturation process in which a resin catalyst is used in the oligomerization zone. A feed stream 10 carries olefins to an oligomerization reactor 14. A modifier stream 12 carrying water inputs into feed stream 10 before entering oligomerization reactor 14. The oligomerization reactor 14 contains a sulfonic acid ion-exchange resin catalyst which promotes the oligomerization of the olefins carried in the feed stream 10 to the oligomerization reactor 14. An effluent stream 16 carries the effluent from the oligomerization reactor 14 to the saturation reactor 18. A heated heavy product recycle stream 20 recycles product to the effluent stream 16 for dissipating heat in the saturation reactor 18. A make-up hydrogen stream 22 is joined to the effluent stream 16 and a recycled hydrogen stream 24 joins effluent stream 16 to provide hydrogen for the saturation reaction in reactor 18. A combined saturation stream 26 carries the oligomerization effluent stream 16 combined with make-up hydrogen stream 22, recycled hydrogen stream 24 and heated heavy product recycle stream 20 to a heater 27 and then into the saturation reactor 18. In the saturation reactor 18, the oligomerization effluent is contacted with hydrogen in the presence of the saturation catalyst of the present invention to effect essentially complete saturation of all olefins, destruction of all oxygenates and conversion of all sulfur compounds to hydrogen sulfide that were carried to the saturation reactor 18 by combined saturation stream 26. The saturation effluent stream 28 carries the saturation effluent to a separator 30 which may comprise a flash drum. The overhead stream 32 from the separator carries very light hydrocarbons and hydrogen for recycling to the saturation reactor 18. Part of the overhead stream 32 is bled off by bleed stream 34 to avoid the buildup of lighter hydrocarbons in the saturation reactor 18. The remainder of the overhead stream 32 is carried by line 36 to a recycle compressor 38 for recycling hydrogen back to the saturation reactor 18 through recycled hydrogen stream 24. The bottoms product stream 40 from the separator 30 carries heavy saturated product oligomers and other components including hydrogen sulfide. The bottoms product stream 40 is split with heavy product recycle stream 44 recycling back to the saturation reactor 18 and distillation influent stream 42 carrying the remaining bottoms product to the distillation column 46. The bleed stream 34 joins distillation influent stream 42 before it enters the distillation column 46. The heavy product recycle stream 44 is heated by heater 48, and heated heavy product recycle stream 20 joins oligomerization effluent stream 16. The bottoms product stream 50 from the distillation column 46 carries essentially completely saturated heavy product oligomers that are an excellent gasoline blending component. The overhead product stream 52 from the distillation column 46 carries essentially completely saturated light hydrocarbons and hydrogen sulfide. The saturation of the light hydrocarbons carried in the overhead product stream 52 is so complete that isobutane in the overhead product stream 52 can be used in processes where the olefin concentration must be less than 0.01 wt-% such as in a tert-butyl hydrogen peroxide reaction, so long as feed stream 10 contains at least approximately 40 wt-% of isobutylene.

Figure 2:
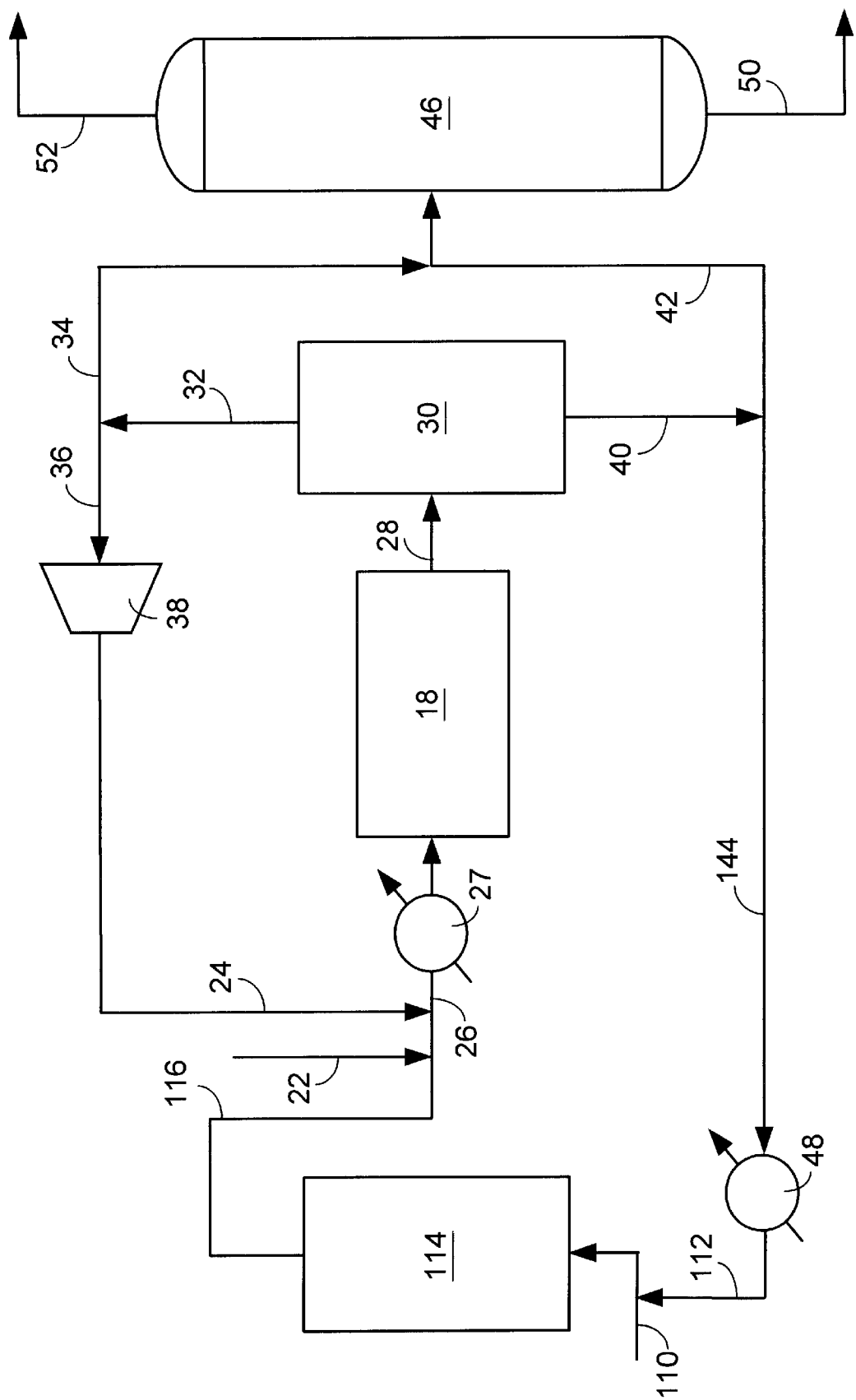
FIG. 2 is an alternative oligomerization process of the present invention.

The invention will now be described with respect to FIG. 2 which illustrates an oligomerization saturation process in which an SPA catalyst is used in the oligomerization zone. The elements in FIG. 2 which are the same in FIG. 1 will retain the reference numeral from FIG. 1. A feed stream 110 carries olefins to an upflow oligomerization reactor 114. A heated heavy paraffinic recycle stream 112 carrying heavy oligomeric products joins feed stream 110 before entering oligomerization reactor 114. The oligomerization reactor 114 contains an SPA catalyst which promotes the oligomerization of the olefins carried in the feed stream 110 in the oligomerization reactor 114. An effluent stream 116 carries the effluent from the oligomerization reactor 114 to the saturation reactor 18. A make-up hydrogen stream 22 is joined to the effluent stream 116 and a recycled hydrogen stream 24 joins effluent stream 116 to provide hydrogen for the saturation reaction in reactor 18. A combined saturation stream 26 carries the oligomerization effluent stream 116 combined with make-up hydrogen stream 22 and recycled hydrogen stream 24 to a heater 27 and then into the saturation reactor 18. In the saturation reactor 18, the oligomerization effluent is contacted with hydrogen in the presence of the saturation catalyst of the present invention to effect essentially complete saturation of all olefins, destruction of all oxygenates and conversion of all sulfur compounds to hydrogen sulfide that were carried to the saturation reactor 18 by combined saturation stream 26. The saturation effluent stream 28 carries the saturation effluent to a separator 30 which may comprise a flash drum. The overhead stream 32 from the separator 30 carries very light hydrocarbons and hydrogen for recycling to the saturation reactor 18. Part of the overhead stream 32 is bled off by bleed stream 34 to avoid the buildup of lighter hydrocarbons in the saturation reactor 18. The remainder of the overhead stream 32 is carried by line 36 to a recycle compressor 38 for recycling hydrogen back to the saturation reactor 18 through recycled hydrogen stream 24. The bottoms product stream 40 from the separator 30 carries heavy saturated product oligomers and other components including hydrogen sulfide. The bottoms product stream 40 is split with heavy paraffinic recycle stream 144 recycling back to the oligomerization reactor 114 and distillation influent stream 42 which carries the remaining bottoms product to the distillation column 46. The bleed stream 34 joins distillation influent stream 42 before it enters the distillation column 46. The heavy paraffinic recycle stream 144 is heated by heater 48, and heated heavy paraffinic recycle stream 112 joins oligomerization feed stream 110. The bottoms product stream 50 from the distillation column 46 carries essentially completely saturated product oligomers that are an excellent gasoline blending component. The overhead product stream 52 from the distillation column 46 carries essentially completely saturated light hydrocarbons and hydrogen sulfide. The saturation of the light hydrocarbons carried in overhead product stream 52 is so complete that isobutane in overhead product stream 52 can be used in processes where the olefin concentration must be less than 0.01 wt-% such as in a tert-butyl hydrogen peroxide reaction, so long as the feed stream 110 comprises at least approximately 40 wt-% isobutylene.

EXAMPLE 1

We ran a pilot plant test to determine the effectiveness of a nickel-molybdenum catalyst in a saturation reactor. We ran a feed of isobutylene spiked with oxygenates as set forth in Table 2.

TABLE 2

| Oxygenate | Concentration (wppm) |
| --- | --- |
| Dimethyl ether | 37 |
| Methanol | 35 |
| Ethanol | 61 |
| Isopropyl alcohol | 9 |
| Acetane | 97 |
| t-Butyl alcohol | 38 |
| t-Butyl formate | 55 |
| t-Butyl acetate | 10 |
| Acetaldehyde | 6 |
| Totals | 398 |

The feed went into an oligomerization reactor that contained SPA catalyst. Hydrogen was added to the effluent from the oligomerization reactor and passed to the saturation reactor. The effluent from the saturation reactor was fed to a stabilizer column where light ends were separated out the overhead and a portion of the bottoms product was recycled with the feed to the oligomerization reactor as a combined feed stream. The remainder of the bottoms product was analyzed as product. The oligomerization reactor was run at 6 hr$^{-1}$ LHSV, 3447 kPa (500 psig) and an inlet temperature of 99° C. (210° F.). The recycled bottoms product was run to the extent that the fresh feed was 25 wt-% of the combined feed stream entering the oligomerization reactor. The saturation reactor was run under the conditions of 8 hr$^{-1}$ LHSV, 2413 kPa (350 psig) and an inlet temperature of 232° C. (450° F.). The bottoms product was analyzed and indicated to have a concentration of 2,2,4-trimethylpentane consistently of at least 80 wt-%. The olefin concentration was predominantly around 0.01 wt-% olefin and rarely exceeded 0.03 wt-% over the course of the run. We found that although some oxygenates survived the oligomerization reactor, no oxygenates were detected in the bottoms product of the stabilization column. The oxygenate detection analysis is accurate down to the 1 ppm level.

EXAMPLE 2

We evaluated seven non-noble metal catalysts having the composition given in Table 3.

TABLE 3

| Catalyst | Composition (wt-%) | | | | | | Sulfide Conditions |
|---|---|---|---|---|---|---|---|
| | Ni | Mo | S | Co | P | Si | |
| 1 | 3.0 | 10.4 | 8.1 | 0 | <0.010 | 0.067 | 775° F./6 hours |
| 2 | 3.7 | 11.8 | 8.0 | 0 | 0.038 | 0.210 | 450° F./24 hours |
| 3 | 3.7 | 11.8 | 7.3 | 0 | 0.038 | 0.210 | 775° F./6 hours |
| 4 | 3.7 | 11.8 | 5.3 | 0 | 0.038 | 0.210 | 450° F./6 hours |
| 5 | 3.0 | 12.0 | 8.6 | 0 | 2.700 | 0.200 | 775° F./6 hours |
| 6 | 0 | 8.0 | 7.1 | 3.0 | 0 | 0.300 | 775° F./6 hours |
| 7 | 3.8 | 16.3 | 13.2 | 0 | N/A | N/A | 775° F./6 hours |

Most of the catalysts were presulfided at 399° C. (750° F.) for 6 hours in the presence of 10 wt-% hydrogen sulfide. A lower sulfiding temperature of 232° C. (450° F.) was also evaluated for 6 and 24 hours for Catalysts 4 and 2, respectively. The catalysts were evaluated in a saturation reactor under conditions of 5 hr$^{-1}$ LHSV, 1724 to 3103 kPa (250 to 450 psig), 177° to 232° C. (350° to 450° F.) and a hydrogen-to-olefin mole ratio of 2.0. The feed was a mixture of $C_8$ and $C_{12}$ olefins blended with the isooctane which is similar to the typical effluent from an SPA $C_4$ olefin oligomerization process. Catalyst 7 was evaluated with a feed that contained mainly $C_{12}$ olefins and some $C_8$ olefins.

Figure 3:
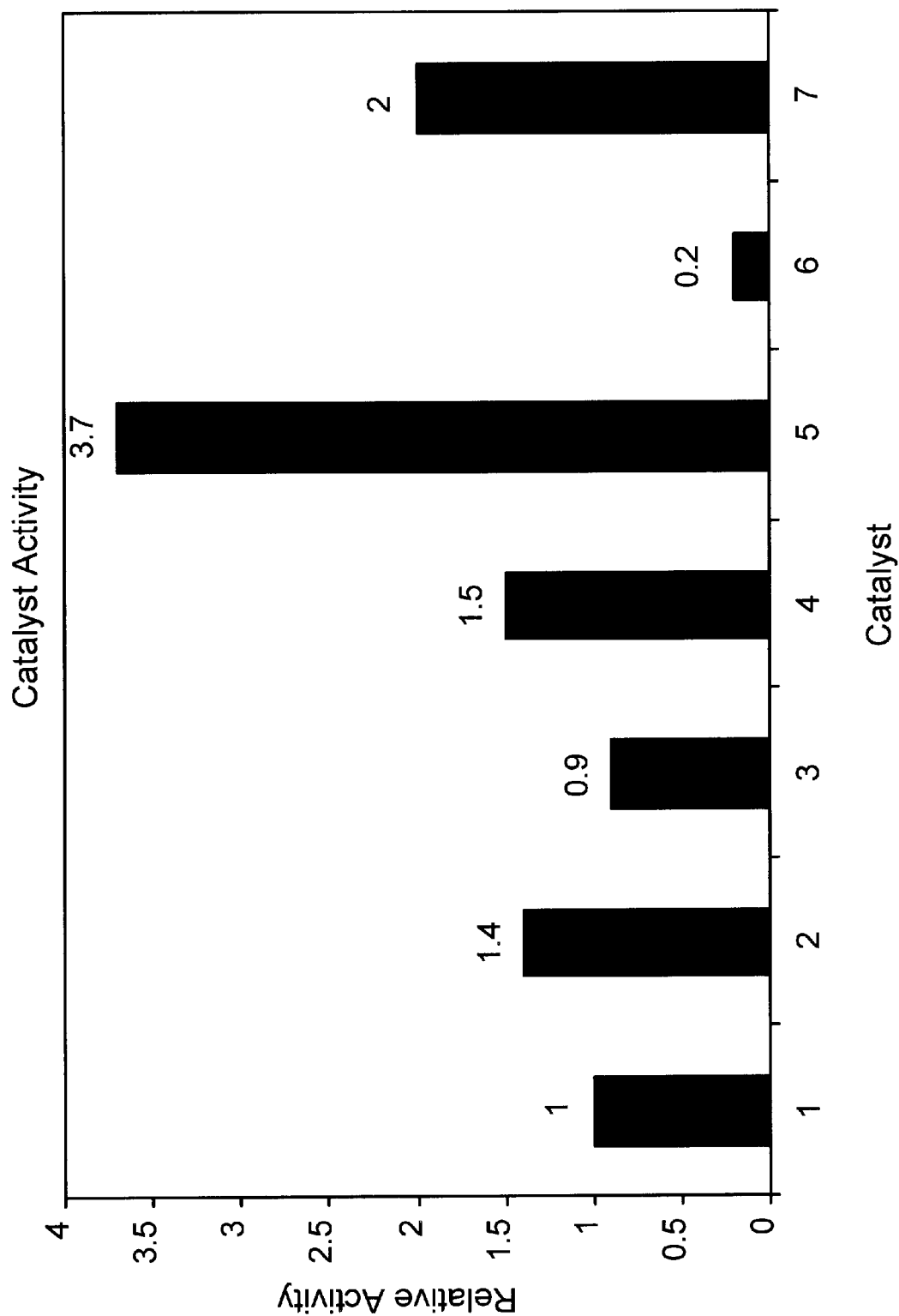
FIG. 3 is a graph comparing the activity of catalysts in the present invention.

FIG. 3 compares the activity of the catalysts evaluated relative to Catalyst 1, with Catalyst 1 having a relative activity of 1. The nickel-molybdenum Catalysts 5 and 7 had higher activity than Catalyst 1 whereas the cobalt-molybdenum Catalyst 6 showed poor activity. Nickel-molybdenum Catalysts 1–4 with low levels of phosphorus and silicon and varying levels of sulfur showed adequate activity with minor differences which can be attributed to the level of sulfur.

Figure 4:
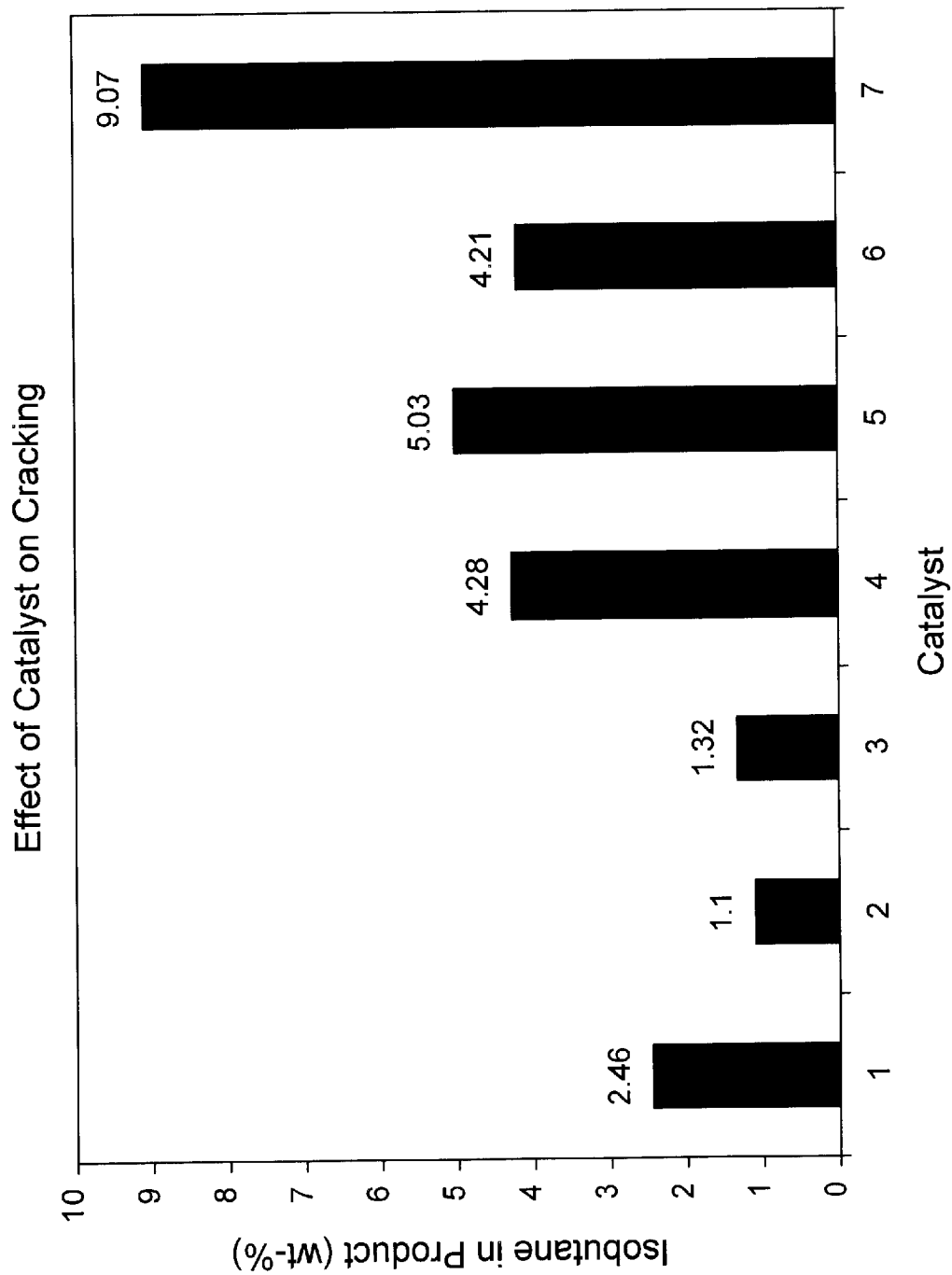
FIG. 4 is a graph comparing the effects of catalysts in the present invention on cracking.

These catalysts were also evaluated for degree of cracking which can be determined from the level of isobutane in the product from the saturation reactor. FIG. 4 shows the effect of the catalyst on cracking in terms of weight percent of isobutane in the product for each catalyst. FIG. 4 shows that nickel-molybdenum Catalyst 7 with a high level of molybdenum exhibited the highest degree of cracking. Moreover, the nickel-molybdenum Catalyst 5 with a moderate level of molybdenum but a relatively high level of phosphorus also exhibited a substantial degree of cracking. The nickel-molybdenum Catalyst 4 with a moderate level of molybdenum and a lower level of phosphorus but with a relatively low level of sulfur also exhibited a high degree of cracking. The nickel-molybdenum catalysts with moderate levels of molybdenum and low levels of phosphorus and silicon and which underwent complete sulfidization exhibited minimal cracking.

What is claimed is:

1. A process for saturating olefins comprising:

feeding a saturation stream containing olefins and oxygenates to a saturation reaction zone, said oxygenates being selected from the group consisting of alcohols, ethers, esters, ketones and aldehydes;

feeding hydrogen to said saturation reaction zone;

contacting said saturation stream with a saturation catalyst comprising a metal from the top row of Group VIII of the Periodic Table of the Elements and a metal from Group VI-B of the Periodic Table of the Elements to saturate said olefins; and recovering an effluent from said saturation reaction zone comprising less than 100 ppm of said oxygenates.

2. The process of claim 1, wherein said saturation effluent contains less than 0.1 wt-% olefins.

3. The process of claim 1, wherein said catalyst contains 5 to 15 wt-% molybdenum.

4. The process of claim 1, wherein said catalyst includes at least 5.5 wt-% sulfur.

5. The process of claim 1, wherein said catalyst includes no more than 0.05 wt-% phosphorus.

6. The process of claim 1, wherein the saturation stream includes sulfur compounds and the saturation effluent comprises less than 1 ppm of any sulfur compound other than hydrogen sulfide.

7. The process of claim 1, wherein the effluent from the saturation reaction zone has a temperature of at least 266° C. (510° F.).

8. The process of claim 1, wherein said saturation stream is provided by passing a feed stream containing light olefins to an oligomerization zone and contacting said feed stream with an oligomerization catalyst to produce heavy olefins.

9. A process for saturating olefins comprising:

feeding a saturation stream containing olefins and oxygenates to a saturation reaction zone;

feeding hydrogen to said saturation reaction zone; and contacting said saturation stream with a saturation catalyst comprising a metal from the top row of Group VIII of the Periodic Table of the Elements and 5–15 wt-% of a metal from Group VI-B of the Periodic Table of the Elements to saturate the olefins.

10. The process of claim 9, wherein said catalyst contains 5 to 15 wt-% molybdenum.

11. The process of claim 9, wherein said catalyst includes at least 5.5 wt-% sulfur.

12. The process of claim 9, wherein said catalyst includes no more than 0.05 wt-% phosphorus.

13. The process of claim 9, wherein the saturation stream includes sulfur compounds and the saturation effluent comprises less than 1 ppm of any sulfur compound other than hydrogen sulfide.

14. The process of claim 9, wherein the effluent from the saturation reaction zone has a temperature of at least 266° C. (510° F.).

15. A process for saturating olefins comprising:

feeding a saturation stream containing olefins, sulfur compounds and oxygenates to a saturation reaction zone;

feeding hydrogen to said saturation reaction zone;

contacting said saturation stream with a saturation catalyst comprising a metal from the top row of Group VIII of the Periodic Table of the Elements, a metal from Group VI-B of the Periodic Table of the Elements and sulfur to saturate said olefins; and recovering an effluent from said saturation reaction zone comprising less than 1 ppm of any sulfur compound other than hydrogen sulfide.

16. The process of claim 15, wherein said catalyst contains 5 to 15 wt-% molybdenum.

17. The process of claim 15, wherein said catalyst includes at least 5.5 wt-% sulfur.

18. The process of claim 15, wherein said catalyst includes no more than 0.05 wt-% phosphorus.

19. The process of claim 15, wherein the effluent from the saturation reaction zone has a temperature of at least 266° C. (510° F.).

* * * * *